United States Patent [19]

Martin et al.

[11] Patent Number: 4,576,960
[45] Date of Patent: * Mar. 18, 1986

[54] 6,11-DIHYDRO-11-OXO-DIBENZ[b,e]OXEPIN DERIVATIVES

[75] Inventors: Lawrence L. Martin, Lebanon; Linda L. Setescak, Somerville, both of N.J.

[73] Assignee: Hoechst Roussel Pharmaceuticals Incorporated, Somerville, N.J.

[*] Notice: The portion of the term of this patent subsequent to May 7, 2002 has been disclaimed.

[21] Appl. No.: 482,072

[22] Filed: Apr. 4, 1983

Related U.S. Application Data

[63] Continuation-in-part of Ser. No. 333,835, Dec. 23, 1981, Pat. No. 4,515,946.

[51] Int. Cl.$^4$ .................. A61K 31/42; A61K 31/335
[52] U.S. Cl. .................................. 514/450; 549/354
[58] Field of Search ................. 549/354; 548/237; 544/96; 424/272, 278, 248.4; 514/450

[56] References Cited

U.S. PATENT DOCUMENTS

| | | | |
|---|---|---|---|
| 4,107,322 | 8/1978 | McFadden et al. | 424/278 |
| 4,118,401 | 10/1978 | McFadden et al. | 260/333 |
| 4,205,170 | 5/1980 | Fujimoto et al. | 424/278 |
| 4,238,620 | 12/1980 | Uno et al. | 424/278 |
| 4,263,437 | 4/1981 | Fujimoto et al. | 424/275 |
| 4,282,365 | 8/1981 | Rokach et al. | 424/278 |
| 4,350,519 | 9/1982 | Dürr | 548/237 |
| 4,356,186 | 10/1982 | Uno et al. | 424/278 |
| 4,377,702 | 3/1983 | Fujimoto et al. | 424/278 |

FOREIGN PATENT DOCUMENTS

| | | | |
|---|---|---|---|
| 0037254 | 10/1981 | European Pat. Off. | 549/354 |
| 0082521 | 6/1983 | European Pat. Off. | |
| 2435613 | 2/1975 | Fed. Rep. of Germany | |
| 124777 | 9/1980 | Japan | |
| 7214977 | 5/1973 | Netherlands | 548/237 |
| 1476214 | 6/1977 | United Kingdom | |
| 1481866 | 8/1977 | United Kingdom | |
| 1538775 | 1/1979 | United Kingdom | |
| 1582191 | 12/1980 | United Kingdom | |

OTHER PUBLICATIONS

Yoshioka et al., Journ. Med. Chem. 1978, vol. 21, No. 7, pp. 633–639.

Soviet Inventions Illustrated Chemical Section, Derwent Publications Ltd., Week B26, 8-8-'79, Sec. C., No. 04662X/03 (SU-662-403).

Primary Examiner—Ethel G. Love
Attorney, Agent, or Firm—Jerome Rosenstock

[57] ABSTRACT

This invention relates to 6,11-dihydro-11-oxo-dibenz[b,e]oxepin derivatives of the formula

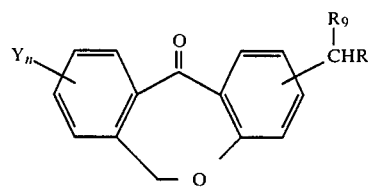

where Y is hydrogen, alkyl, alkoxy, halogen and trifluoromethyl, n is 0, 1, 2 or 3; $R_9$ is hydrogen and alkyl; R is

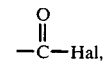

where Hal is a halogen;

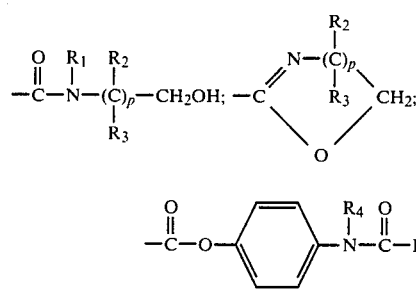

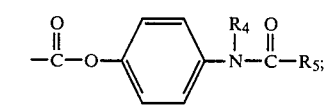

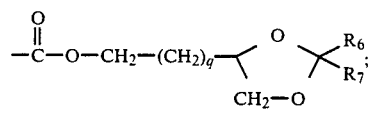

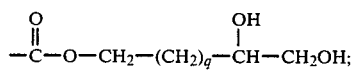

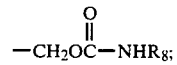

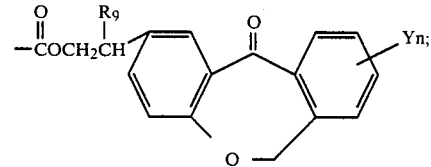

where $R_{10}$ is hydrogen, alkyl and benzyl of the formula

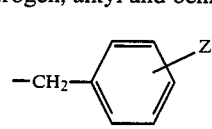

where Z is hydrogen, alkyl, alkoxy, halogen, trifluoromethyl, nitro, and amino; where n is 0, 1, 2 or 3; p is 1 or 2; q is 0, 1 or 2; $R_1$ to $R_7$ are the same or different and are hydrogen and alkyl; and $R_8$ is hydrogen, alkyl and phenyl; and $R_9$ is hydrogen and alkyl, and where appropriate pharmaceutically acceptable acid or base addition salts thereof.

17 Claims, No Drawings

6,11-DIHYDRO-11-OXO-DIBENZ[B,E]OXEPIN DERIVATIVES

This application is a continuation-in-part of application Ser. No. 333,835, filed Dec. 23, 1981, now U.S. Pat. No. 4,515,946.

To the best of our knowledge, the compounds of the present invention have not heretofor been described or suggested. 6,11-Dihydro-dibenz[b,e]oxepin-acetic acids and derivatives having the general formula

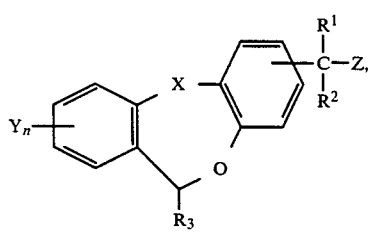

where X is C=O, CHCl, CHBr, $CH_2$ or $CHOR^4$; Y is alkyl or alkoxy of 1 to 4 carbon atoms, halogen or trifluoromethyl; n is 0, 1, 2 or 3; Z is $COOR^5$, $CH_2OR^5$, $CONHR^5$, $CONR_2^5$ or $CONHOR^5$; and $R^1$-$R^5$ are hydrogen or alkyl of 1 to 4 carbon atoms are described by G. C. Helsley et al. in U.S. patent application Ser. No. 459,774, filed Apr. 10, 1974, are outside the scope of this invention. The same applies to dibenzoxepin derivatives of the formula

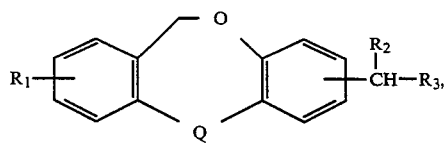

where $R_1$ represents a hydrogen atom, a halogen atom, a trihalomethyl group or a lower alkoxy group; $R_2$ represents a hydrogen atom or a lower akyl group; $R_3$ represents a carboxyl group, a lower alkoxycarbonyl group, a hydroxy methyl group, a lower alkoxy methyl group or a lower acyloxy methyl group; and Q represents a methylene group, a hydroxymethylene group or a carbonyl group; described by K. Ueno et al., U.S. application Ser. No. 491,434 filed July 24, 1974, now abandoned. Additional compounds of this type, where $R_1$ additionally includes alkyl, e.g. methyl, and nitro are described in Ueno et al., Journal of Medicinal Chemistry, Vol. 19, No. 7, 941 (1976).

The compounds of the present invention have the general formula

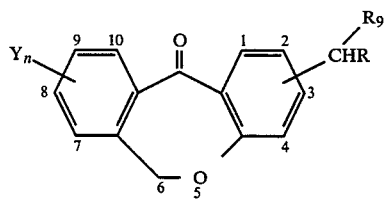

where Y is alkyl, alkoxy, halogen and trifluoromethyl, n is 0, 1, 2 or 3; $R_9$ is hydrogen and alkyl; R is

where Hal is halogen;

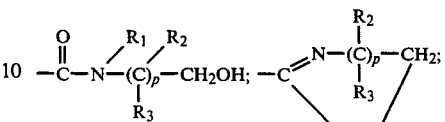

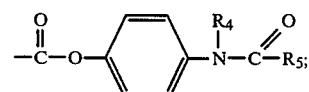

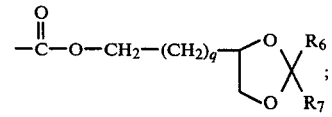

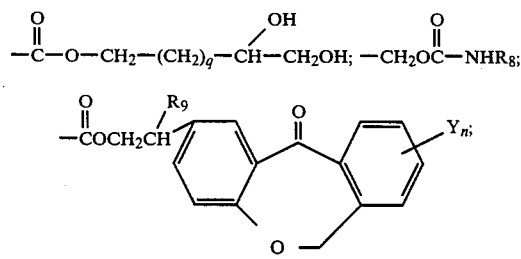

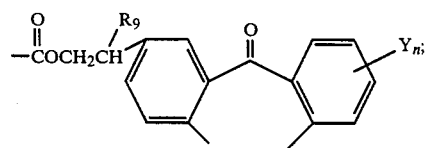

, where $R_{10}$ is hydrogen, alkyl and benzyl of the formula

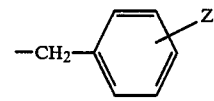

where Z is hydrogen, alkyl, alkoxy, halogen, trifluoromethyl, nitro and amino; where n is 0, 1, 2 or 3; p is 1 or 2; q is 0, 1 or 2; $R_1$ to $R_7$ are the same or different and are hydrogen and alkyl, $R_8$ is hydrogen, alkyl and phenyl; and where appropriate the optical isomers thereof and the racemic mixture thereof and the pharmaceutically acceptable acid or base addition salts thereof.

In the above definitions the terms "alkyl", "alkoxy", mean the group it is describing contains from 1 to 4 carbon atoms. The term "alkyl" refers to a straight or branched chain hydrocarbon containing no unsaturation e.g. methyl, ethyl, propyl, 2-butyl, etc. The term "alkoxy" refers to a monovalent substituent which consists of an alkyl group linked through an ether oxygen having its free valence bond from the ether oxygen e.g. methoxy, ethoxy, propoxy, isobutoxy etc. The term "halogen" refers to a member of the family consisting of fluorine, chlorine, bromine and iodine. The term "alkylene" refers to a bivalent radical of the branched or unbranched alkyl group, having from 1 to 4 carbon atoms, from which it is derived from having valence bonds from two terminal carbons thereof, e.g. methylene (—CH$_2$—), ethylene (—CH$_2$CH$_2$—), propylene (—CH$_2$CH$_2$CH$_2$—), isopropylene (—CH$_2$—CH—), etc.

The compounds of the present invention are prepared in the following manner. The substituents R$_9$, R$_{10}$, R, R$_1$ to R$_8$, Y and Z and the members n, p, and q are as defined earlier.

A 6,11-dihydro-11-oxodibenz[b,e]oxepin acetic acid is employed of the structural formula

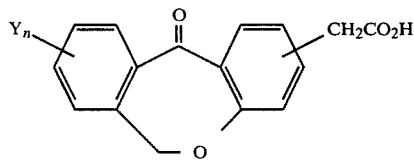

or of the structural formula II

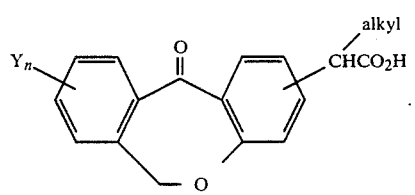

Such acetic acids are prepared generally in the manner described in British Patent Specification No. 1,481,866; British Patent Specification No. 1,538,775, and Ueno et al., *Journal of Medicinal Chemistry*, Vol. 19, No. 7, 941 (1976), all incorporated hereinto by reference.

For example, typically a compound of the general formula

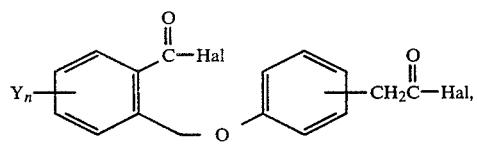

is reacted with a Friedel-Crafts catalyst, e.g. AlCl$_3$, SnCl$_4$, FeCl$_3$, etc. at a typical temperature of 0° C. to ambient, to form Compound I.

Compound II is prepared generally in the manner described in British Patent Specification No. 1,481,866; British Patent Specification No. 1,538,775 and Ueno et al., *Journal of Medicinal Chemistry*, Vol. 19, No. 7, 941 (1976). For example, typically a phthalide of the formula

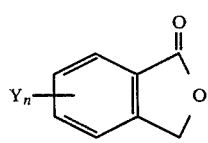

is condensed under conventional conditions, e.g. by heating with a phenol of the formula

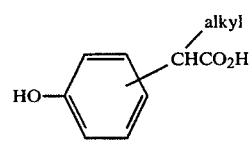

to yield compound (V) of the formula

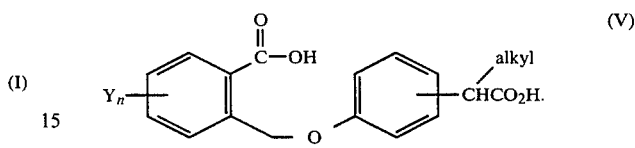

The resulting Compound (V) is then cyclized with a conventional cyclization agent, e.g. polyphosphoric ester from P$_2$O$_5$ and ethanol, polyphosphoric acid from H$_3$PO$_4$ and P$_2$O$_5$, etc. to form Compound II.

Compound I or Compound II is converted in a conventional manner to an acyl halide of the structural formula

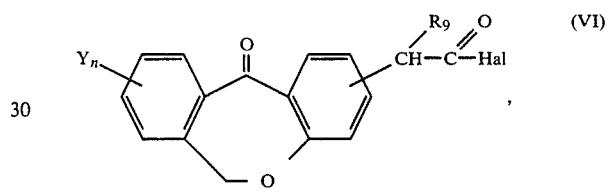

where Hal is a halogen. Typically, such conversion is carried out by reaction with an inorganic halide such as for example phosphorus trihalide or pentahalide or thionyl chloride.

Compound VI is reacted with an alcohol substituted amine of the structural formula

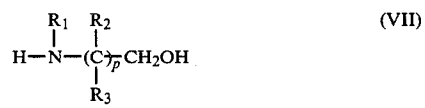

in a suitable inert solvent, e.g. methylene chloride, at a typical temperature of 0° C. to 25° C., for 0.1 to 12 hours to form a compound of the invention having the structural formula

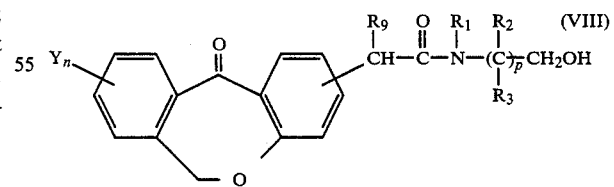

Compound (VIII) can be treated with a conventional dehydrating agent e.g., an acidic dehydrating agent such as thionyl chloride, etc., typically at 0° C. to 25° C., preferably from 0° to 10° C., for a time period of from 2 to 3 minutes to about 12 hours, to form a 5 or 6 membered ring system substituent of a compound of the invention having the structural formula

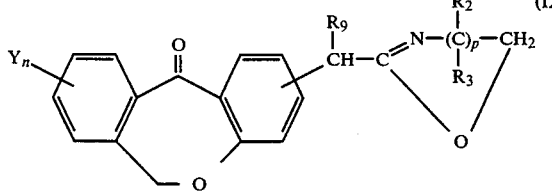

The acyl halide (VI) is reacted with an amido substituted phenol of the structural formula

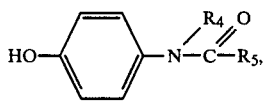

in a suitable solvent, e.g. pyridine, at a typical temperature ranging from 0° to 90° C., for 0.1 to 2 hours to form a compound of the invention having the structural formula of (XI)

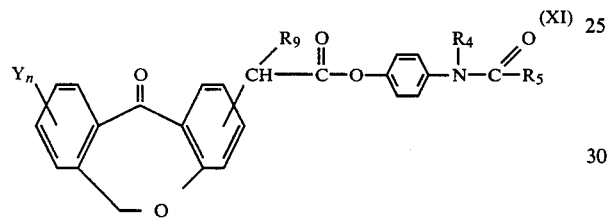

A acyl halide (VI) is reacted with a dioxalane substituted alcohol, having the structural formula of

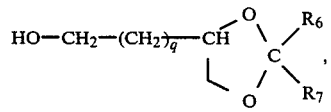

in a suitable basic solvent (acid scavenger) such as for example pyridine, etc. at a temperature of 0° to 30° C. for a period of time of 0.5 to 12 hours, to form a compound of the invention having the structural formula of

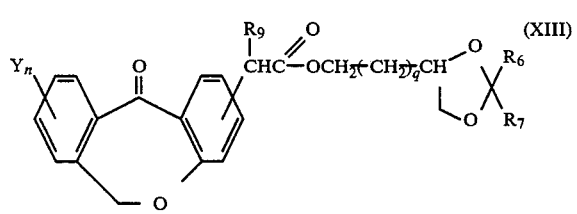

Compound (XIII) can be hydrolyzed in a conventional manner e.g. in the presence of an acid, to form a diol or a glyceride of the invention having the structural formula of

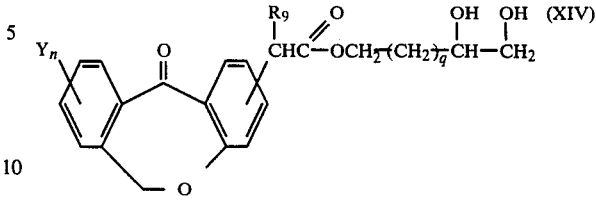

The 6,11-dihydro-11-oxo-dibenz[b,e]oxepin acetic acid, Compound I or Compound II may be reduced using conventional means and techniques, as for example by treatment with borane or borane dimethylsulfide to form an alcohol having the structural formula of

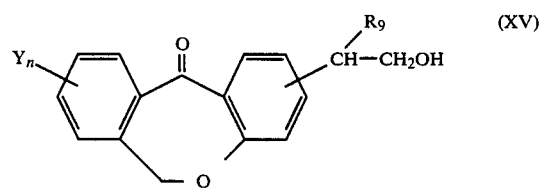

This alcohol is treated with an isocyanate having the structural formula of $O=C=N-R_8$ (XVI), typically in a moisture free solvent at a temperature ranging from ambient to reflux temperature of the solvent to form a carbamate derivative of the invention having the structural formula of

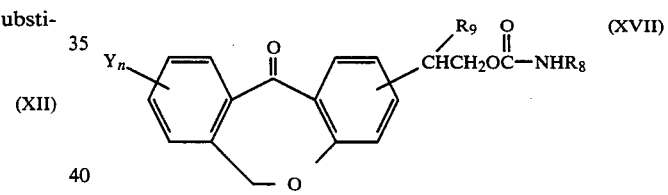

The acyl halide of the invention, Compound (VI), is reacted with the alcohol, Compound (XV), in a conventional manner in the presence of an acid scavenger, e.g. pyridine, to form a compound of the invention having the structural formula

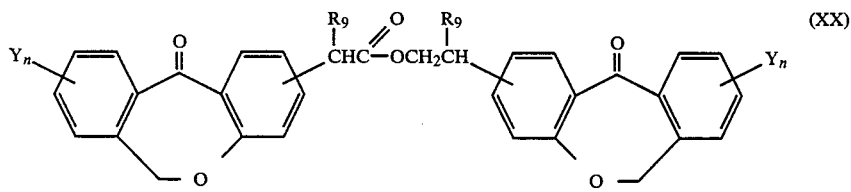

Compound I or Compound II is reacted under conventional nucleophilic substitution reaction conditions, e.g., in the presence of base, with an alkyl halo acetate of the formula

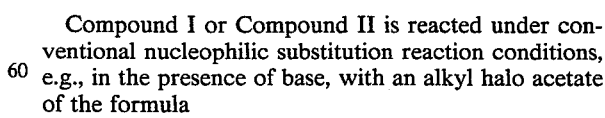

to form a compound of the invention having the structural formula

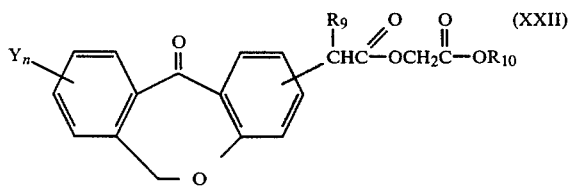

Where $R_{10}$ is

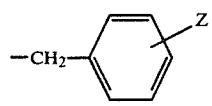

the corresponding Compound XXIII may be subjectd to hydrogenolysis under conventional conditions, e.g. Pd on carbon, to form Compound XXII where $R_{10}$ is hydrogen.

The compounds of the present invention are useful as antiinflammatory agents due to their ability to suppress inflammation in mammals. The activity of the compounds is demonstrated in the carrageenin induced rat paw edema antiinflammatory assay [Proc. Soc. Exptl. Biol. Med., III 544 (1962), J. Pharmacol. Exp. Ther., 141 (1963)]. For example, at oral doses of 20.7, 27.5, 7.7, 32.3, 14.1 and 50 mk/kg the compounds 2-(6,11-dihydro-11-oxodibenz[b,e]oxepin-2-yl)ethanol, 2-(6,11-dihydro-11-oxodibenz[b,e]oxepin-2-yl)ethyl propionate, 2-(6,11-dihydro-11-oxodibenz[b,e]oxepin-2-yl)ethyl acetate, 2-methoxy-2-oxoethyl 6,11-dihydro-α-methyl-11-oxodibenz[b,e]oxepin-2-acetate and carboxy methyl 6,11-dihydro-α-methyl-11-oxodibenz[b,e]oxepin-2-acetate hemihydrate respectively exhibit an approximately 50% inhibition of edema, whereas 2-phenylmethoxy-2-oxoethyl 6,11-dihydro-α-methyl-11-oxodibenz[b,e]oxepin-2-acetate exhibits 43% inhibition of edema at an oral dose of 20 mg/kg.

The compounds of the invention compare favorably with the well-known antiinflammatory compound phenylbutazone which, in a similar test exhibited analogous activity of edema at an oral dose of 50 mg/kg.

Compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. For example, at doses of 7.7, 5.2, and 6.6 mg/kg, the compounds 2-(6,11-dihydro-11-oxodibenz[b,e]oxepin-2-yl)ethyl acetate, (±) 1-(6,11-dihydro-11-oxodibenz[b,e]oxepin-2-acetyl)-glyceride and (±) (2,2-dimethyl-1,3-dioxolan-4-yl)methyl (6,11-dihydro-11-oxodibenz[b,e]oxepin-2-yl)acetate, respectively, exhibit an approximately 50% inhibition of writhing. Additionally, at oral doses of 2.9, 1.1 and 2.3 mg/kg the compounds 2-phenylmethoxy-2-oxoethyl 6,11-dihydro-α-methyl-11-oxodibenz[b,e]oxepin-2-acetate, 2-methoxy-2-oxoethyl 6,11-dihydro-α-methyl-11-oxodibenz[b,e]oxepin-2-acetate and carboxy methyl 6,11-dihydro-α-methyl-11-oxodibenz[b,e]oxepin-2-acetate hemihydrate, respectively, exhibit $ED_{50}$ inhibition of writhing. These data illustrate that compounds of this invention are useful as antiinflammatory and analgesic agents at the dose of 5 to 50 mg/kg of body weight.

The compounds of the invention compare favorably with the well-known analgesic compound indomethacin, which, in a similar test exhibits an $ED_{50}$ inhibition of writhing at an oral dose of 0.7 mg/kg.

Effective amounts of the compounds of the present invention may be administered to a subject by one of various methods, for example, orally as in capsules or tablets, parenterally in the form of sterile solutions. The compounds of the invention, while effective themselves, may be formulated where appropriate and administered in the form of their pharmaceutically acceptable acid e.g., HCl, etc. addition salts or base, e.g. $Na^+$, $K^+$, $Ca^{++}$, etc. addition salts for purposes of stability, convenience of crystallization, increased solubility and the like.

The compounds of the present invention may be prepared and administered as an antiinflammatory or analgesic pharmaceutical composition or mixture comprising the compound as an active component thereof and at least an inert material, e.g. an adjuvant, diluent, etc., as a second component thereof.

The compounds of the present invention may be administered orally, for example, with an inert diluent or with an edible carrier. They may be enclosed in gelatin capsules or compressed into tablets. For the purpose of oral therapeutic administration, the compounds may be incorporated with elixirs, suspensions, syrups, wafers, chewing gums and the like. These preparations should contain at least 4% of the 6,11-dihydro-11-oxodibenz[b,e]oxepin derivatives of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the 6,11-dihydro-11-oxodibenz[b,e]oxepin derivatives of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 6,11-dihydro-11-oxodibenz[b,e]oxepin derivatives of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 6,11-dihydro-11-oxodibenz[b,e]oxepin derivatives of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

2-(6,11-Dihydro-11-oxodibenz[b,e]oxepin-2-yl)ethanol

A stirred solution ($-17°$ C.) of 6.71 g (0.025 mol) of 6,11-dihydro-11-oxodibenz[b,e]oxepin-2-acetic acid and 18 ml of anhydrous tetrahydrofuran was treated dropwise over 15 minutes with 24 ml of 1.06M borane in tetrahydrofuran solution (approximately 0.025 mol $BH_3$). After total addition, the cooling bath was allowed to equilibrate overnight (about 16 hours) to ambient temperature. The resultant stirred, chilled (5° C.) solution was treated with 5 ml of methanol, diluted with 50 ml of water and concentrated on a rotary evaporator at 40° C. to remove the organic solvents. The residue was diluted with water (70 ml) and $CH_2Cl_2$ (70 ml) and was washed with 5% $NaHCO_3$ solution until the aqueous phase had a pH of 8. The organic phase was dried ($Na_2SO_4$) and then filtered. The resultant organic phase was concentrated to an oil (5.51 g) which was dried by azeotropic distillation of toluene (70 ml). A portion of the oil was dissolved in 8 ml of anhydrous ethyl acetate, diluted to the cloud point with hexane (7 ml) and was then treated dropwise with ethyl acetate (0.6 ml) until a clear solution was obtained. The solution was subjected to high pressure liquid chromatography with hexane/ethyl acetate (60:40). The product-containing fractions were combined and concentrated to an oil (2.08 g). On standing at 5° C., some crystals formed and were stirred into the oil. On trituration of the mixture with hexane the oil solidified. The material was isolated by vacuum filtration, washed with hexane and dried in vacuo at ambient temperature to afford 1.42 g (22.3%) of a solid of 2-(6,11-dihydro-11-oxodibenz[b,e]oxepin-2-yl)ethanol, m.p. 78°–81.5° C.

ANALYSIS: Calculated for $C_{16}H_{14}O_3$: 75.57%C; 5.55%H; Found: 75.73%C; 5.56%H

EXAMPLE 2

6,11-Dihydro-N-(1-hydroxy-2-methyl-2-propyl)-11-oxodibenz[b,e]oxepin-2-yl acetamide A water cooled stirred suspension of 13.41 g (0.05 mol) of 6,11-dihydro-11-oxodibenz[b,e]oxepin-2-yl acetic acid, 50 ml of sieve-dried methylene chloride and three drops of dimethylformamide was treated for a few minutes with 6.54 g (0.055 mol) of thionyl chloride. After total addition the suspension was stirred 15 minutes with cooling and was then intermittently warmed until the evolution of HCl ceased. A stirred ice water chilled solution of 13.37 g (0.15 mol) of 2-amino-2-methyl-1-propanol and 50 ml of sieve-dried methylene chloride was treated dropwise over 0.5 hour with the acid chloride solution. After total addition the resultant suspension was stirred with cooling for 20 minutes and was then stirred 1.5 hours at ambient temperature. The suspension was vacuum filtered and the filtrate was washed with 100 ml each of 5% HCl, water, and 5% $Na_2CO_3$. The organic phase was dried by extracting with 500 ml of saturated NaCl solution and then over anhydrous $Na_2SO_4$. The resultant mixture was filtered and the filtrate was concentrated to an oil which was dried by azeotropic distillation of absolute ethanol to afford 14.3 g (84.3%) of a crude product. Two recrystallizations from benzene and a final recrystallization from isopropanol afforded 7.0 g (41.2%) of crystals of 6,11-dihydro-N-(1-hydroxy-2-methyl-2-propyl)-11-oxodibenz[b,e]oxepin-2-yl acetamide, m.p. 132°–134° C.

ANALYSIS: Calculated for $C_{20}H_{21}NO_4$: 70.78%C; 6.24%H; 4.13%N; Found: 70.69%C; 6.26%H; 3.96%N

EXAMPLE 3

6,11-Dihydro-11-oxodibenz[b,e]oxepin-2-acetyl chloride

A stirred, cooled suspension of 40.23 g (0.15 mol) of 6,11-dihydro-11-oxodibenz[b,e]oxepin-2-acetic acid, 150 ml of sieve dried $CH_2Cl_2$ and 3 drops of dimethylformamide was treated for a few minutes with 19.62 g (0.165 mol) of thionyl chloride. After total addition the suspension was stirred for 30 minutes with cooling. The suspension was then intermittently warmed until gas evolution ceased. The resultant solution was cooled and concentrated to an oil which crystallized on trituration with hexane to afford 41.96 g of a crude material. Recrystallization from 100 ml of $CCl_4$ afforded 36.7 g (85.2%) of crystals of 6,11-dihydro-11-oxodibenz[b,e]oxepin-2-acetyl chloride, m.p. 95°–98.5° C.

ANALYSIS: Calculated for $C_{16}H_{11}ClO_3$: 67.03%C; 3.87%H; Found: 67.57%C; 4.09%H

EXAMPLE 4

2-(6,11-Dihydro-11-oxodibenz[b,e]oxepin-2-yl)ethyl propionate

A stirred solution of 6.36 g (0.025 mol) of 2-(6,11-dihydro-11-oxodibenz[b,e]oxepin-2-yl)ethanol of Example 1 and 25 ml of KOH-dried pyridine was treated dropwise over one minute with 9.76 g (0.075 mol) of propionic anhydride with exclusion of moisture. After total addition, the solution was stirred 3.5 hours at ambient temperature and then quenched by decanting into 150 ml of ice water. The solution was treated with 100 ml of ether and acidified with 5% hydrochloric acid. The organic phase was washed twice with 5% HCl, 5% $NaHCO_3$ and water. The dried ($Na_2SO_4$) organic phase was concentrated to an oil (7.28 g). After standing 24 hours at ambient temperature, crystallization was initiated. The oil was triturated with hexane until crystallization was complete. The solid was collected by vacuum filtration, washed with hexane and dried to afford 6.71 g (86.5%) of crystals of 2-(6,11-dihydro-11-oxodibenz[b,e]oxepin-2-yl)ethyl propionate, m.p. 71.5°–73.5° C.

ANALYSIS: Calculated for $C_{19}H_{18}O_4$: 73.53%C; 5.85%H; Found: 73.33%C; 5.93%H

EXAMPLE 5

2-(6,11-Dihydro-11-oxodibenz[b,e]oxepin-2-yl)ethyl acetate

A stirred solution of 5.08 g (0.02 mol) of 2-(6,11-dihydro-11-oxodibenz[b,e]oxepin-2-yl)ethanol of Example 1 and 25 ml of KOH-dried pyridine was treated over one minute with 6.12 g (0.06 mol) of acetic anhydride. The solution was stirred at ambient temperature for four hours, warmed for five minutes and decanted into 200 ml of ice water. The mixture was extracted with 200 ml of $CH_2Cl_2$ and the organic phase was washed with a total of 500 ml of 5% hydrochloric acid solution and 100 ml of water. The dried ($Na_2SO_4$) organic phase was evaporated to a cloudy oil which was subjected to azeotropic distillation with benzene. Final traces of solvent were removed in vacuo (pump) at 40° C. and the residual oil was refrigerated during which the oil crystallized. The solid was triturated with hexane and isolated by vacuum filtration to afford 4.39 g (74.0%) of crystals of 2-(6,11-dihydro-11-oxodibenz[b,e]oxepin-2-yl)ethyl acetate, m.p. 55°–58° C.

ANALYSIS: Calculated for $C_{18}H_{16}O_4$: 72.96%C; 5.44%H; Found: 72.87%C; 5.45%H

EXAMPLE 6

2-(6,11-Dihydro-11-oxodibenz[b,e]oxepin-2-yl)methyl-4,4-dimethyloxazoline

A stirred, ice water cooled mixture of 10.25 g (0.0302 mol) of 6,11-dihydro-N-(1-hydroxy-2-methyl-2-propyl)-11-oxodibenz[b,e]oxepin-2-yl acetamide of Example 2, and 100 ml of sieve dried $CH_2Cl_2$ was treated dropwise over a few minutes with 3.95 g (0.0332 mol) of thionyl chloride. The solution was then stirred 15 minutes with cooling and overnight (about 16 hours) at ambient temperature. The solution was washed with 10% sodium hydroxide solution, dried ($Na_2SO_4$) and concentrated to an oil which was dried by azeotropic distillation of toluene. On standing overnight at 5° C. the oil crystallized. Recrystallization from 12 ml of isopropanol afforded 6.10 g (62.9%) of crystals of 2-(6,11-dihydro-11-oxodibenz[b,e]oxepin2-yl)methyl-4,4-dimethyloxazoline, m.p. 101°–103.5° C.

ANALYSIS: Calculated for $C_{20}H_{19}NO_3$: 74.75%C; 5.96%H; 4.36%N; Found: 74.80%C; 5.90%H; 4.23%N

EXAMPLE 7

2-(6,11-Dihydro-11-oxodibenz[b,e]oxepin-2-yl)ethyl (6,11-dihydro-11-oxodibenz[b,e]oxepin-2-yl)acetate A stirred ice-water chilled solution of 5.08 g (0.02 mol) of 2-(6,11-dihydro-11-oxodibenz[b,e]oxepin-2-yl)ethanol of Example 1, 11 ml of KOH-dried pyridine and 10 ml of sieve dried $CH_2Cl_2$ was treated over ten minutes with a solution of 6.31 g (0.022 mol) of 6,11-dihydro-11-oxodibenz[b,e]oxepin-2-acetyl chloride of Example 3. After total addition the solution was stirred for one hour with cooling and then one hour at ambient temperature. Aqueous quenching, extraction with $CH_2Cl_2$ and washing with 5% HCl, water, and 5% $NaHCO_3$ afforded 8.74 g of a foam which was a mixture of the starting alcohol and the desired ester. A cooled solution of the foam, 10 ml of KOH-dried pyridine and 10 ml of $CH_2Cl_2$ was treated over a few minutes with a solution of 3.15 g (0.011 mol) of the acid chloride (Example 3) and 10 ml of $CH_2Cl_2$. After total addition the solution was stirred overnight (about 16 hours) at ambient temperature and was quenched and extracted as previously described to afford 9.39 g of a powder after azeotropic distillation of toluene. The material was purified by high pressure liquid chromatography using 1% ethyl acetate in $CH_2Cl_2$ to afford 5.82 g of a viscous oil. The oil was purified again by high pressure liquid chromatography to afford 2.61 g (25.9%) of a tacky amorphous solid of 2-(6,11-dihydro-11-oxodibenz[b,e]oxepin-2-yl)ethyl (6,11-dihydro-11-oxodibenz[b,e]oxepin-2-yl)acetate after vacuum drying at 60°–100° C.

ANALYSIS: Calculated for $C_{32}H_{24}O_6$: 76.18%C; 4.79%H; Found: 76.19%C; 5.17%H

EXAMPLE 8

4-Acetamidophenyl(6,11-dihydro-11-oxodibenz[b,e]oxepin-2-yl-acetate

A stirred, ice water chilled solution of 6.04 g (0.04 mol) of 4-acetamidophenol and 30 ml of sieve dried pyridine was treated over one minute with 17.20 g (0.06 mol) of 6,11-dihydro-11-oxodibenz[b,e]oxepin-2-acetyl chloride of Example 3. The mixture was stirred with cooling for a few minutes, stirred at ambient temperatures for 25 minutes and warmed for 1.5 hours on a steam bath. The solution was poured into 150 ml of water and the aqueous phase was decanted. The resultant viscous oil was washed with 150 ml of water and dissolved in 150 ml of $CH_2Cl_2$. The solution was washed sequentially with 5% HCl, water, 5% $NaHCO_3$ and water. The dried ($Na_2SO_4$) organic phase was concentrated to an oil which solidified on trituration with anhydrous ether to afford 16.80 g of a crude material. Recrystallization of a 1.0 g sample from acetonitrile afforded 0.23 g of a solid of 4-acetamidophenyl(6,11-dihydro-11-oxodibenz[b,e]oxepin-2-yl-acetate, m.p. 162°–168° C. The total yield was 4.58 g (28.5%).

ANALYSIS: Calculated for $C_{24}H_{19}NO_5$: 71.81%C; 4.77%H; 3.49N; Found: 72.10%C; 4.66%H; 3.35%N

EXAMPLE 9

(±)(2,2-Dimethyl-1,3-dioxolan-4-yl)methyl(6,11-dihydro-11-oxodibenz[b,e]oxepin-2-yl)acetate A stirred solution of 13.22 g (0.01 mol) of (±)(2,2-dimethyl-1,3-dioxolan-4-methanol, 8.70 g (0.11 mol) of KOH-dried pyridine and 200 ml of anhydrous tetrahydrofuran was treated dropwise over 0.5 hours with a solution of 28.67 g (0.1 mol) of 6,11-dihydro-11-oxodibenz[b,e]oxepin-2-acetyl chloride of Example 3 and 150 ml of anhydrous tetrahydrofuran. During the addition, a colorless precipitate separated. After stirring overnight (about 16 hours) at ambient temperature with exclusion of moisture, the mixture was vacuum filtered and the filtrate was concentrated to an oil. A solution of the oil and 250 ml of ether was washed with 5% $NaHCO_3$ (150 ml) and water (150 ml), dried ($Na_2SO_4$), filtered and concentrated to an oil. The oil was further dried by azeotropic distillation with toluene. Residual toluene was removed at 60° C. in vacuo (pump) to afford 32.21 g (84.2%) of an oil of (±)(2,2-dimethyl-1,3-dioxolan-4-yl)methyl(6,11-dihydro-11-oxodibenz[b,e]oxepin-2-yl)acetate.

ANALYSIS: Calculated for $C_{22}H_{22}O_6$: 69.10%C; 5.80%H; Found: 69.34%C; 5.82%H

EXAMPLE 10

(±)1-(6,11-Dihydro-11-oxodibenz[b,e]oxepin-2-acetyl)-glyceride

A stirred solution of 6.85 g (0.018 mol) of (±)(2,2-dimethyl-1,3-dioxolan-4-yl)methyl-(6,11-dihydro-11-oxodibenz[b,e]oxepin-2-yl)acetate of Example 9 and 30 ml of acetone was treated with 8 ml of dilute aqueous hydrochloric acid solution. The solution was stirred 2.3 hours at ambient temperature and was then concentrated on a rotary evaporator. The residue was partitioned between 100 ml of water and 350 ml of ether. The organic phase was washed with water and 5% sodium bicarbonate solution, dried ($Na_2SO_4$) and concentrated to an oil (6.11 g). The oil was combined with 4.3 g of similarly prepared oil and 20 ml of ethyl acetate. The solution was subjected to high pressure liquid chromatographic purification. The product containing fractions were combined and concentrated to an oil of (±)1-(6,11-dihydro-11-oxodibenz[b,e]oxepin-2-acetyl)-glyceride which was dried in vacuo at 80° C. to remove residual solvent (yield 5.09 g, 48.4%).

ANALYSIS: Calculated for $C_{19}H_{18}O_6$: 66.67%C; 5.30%H; Found: 66.49%C; 5.34%H

EXAMPLE 11

2-(6,11-Dihydro-11-oxodibenz[b,e]oxepin-2-yl)ethyl carbanilate

A stirred solution of 2.54 g (0.01 mol) of 2-(6,11-dihydro-11-oxodibenz[b,e]oxepin-2-yl)ethanol of Example 1, 20 ml of sieve dried $CH_2Cl_2$ and 1.55 g (0.013 mol) of phenylisocyanate was heated 20 hours under reflux with exclusion of moisture. The cooled solution was concentrated on a rotary evaporator to afford an oil which was dissolved in 10 ml of hot toluene. The solution was seeded with product (previously obtained by the method described herein), stirred until a thick suspension formed and allowed to stand overnight (about 16 hours) at ambient temperature. Filtration and drying in vacuo afforded 2.53 g (67.8%) of a colorless solid of 2-(6,11-dihydro-11-oxodibenz[b,e]oxepin-2-yl)ethyl carbanilate, m.p. 98°–99° C.

ANALYSIS: Calculated for $C_{23}H_{19}NO_4$: 73.98%C; 5.13%H; 3.75%N; Found: 73.70%C; 5.09%H; 3.88%N

EXAMPLE 12

Methyl(6,11-dihydro-11-oxodibenz[b,e]oxepin-2-yl)acetoxyacetate

A mixture of 15 g (0.052 m) of 6,11-dihydro-11-oxodibenz[b,e]oxepin-2-acetic acid in 100 ml of dimethylformamide and 3.87 g (0.028 m) of $K_2CO_3$ was warmed to an internal temperature of 50° C. in an atmosphere of nitrogen for 1.5 hours. To this mixture, 9.41 g (0.062 m) of methyl bromoacetate was added dropwise and the mixture was held at 50° C. overnight. The reaction mixture was poured into water and extracted with ether. The ether extract was washed with 5% $NaHCO_3$ and water, dried over $Na_2SO_4$, filtered and evaporated to give 16.5 g (94%) of an oil of methyl(6,11-dihydro-11-oxodibenz[b,e]oxepin-2-yl)acetoxyacetate.

ANALYSIS: Calculated for $C_{19}H_{16}O_6$: 67.05%C; 4.74%H; Found: 66.88%C; 4.74%H

EXAMPLE 13

(±)-2-Phenylmethoxy-2-oxoethyl 6,11-dihydro-6-methyl-11-oxodibenz[b,e]oxepin-2-acetate A mixture of 7.09 g (0.025 m) of 6,11-dihydro-α-methyl-11-oxodibenz[b,e]oxepin-2-acetic acid, and 2.59 g (0.0188 m) of anhydrous $K_2CO_3$ in 70 ml of dimethylformamide was warmed at 50° C. for one hour in an atmosphere of nitrogen. To this mixture 6.32 g (0.276 m) of benzyl bromoacetate was added dropwise and the mixture was held at 50° C. overnight (about 16 hours). The reaction mixture was poured into water and extracted with ether. The ether extract was washed with 5% $NaHCO_3$, dried over $Na_2SO_4$, filtered and evaporated to give 10.11 g (94%) of an oil of (±)-2-phenylmethoxy-2-oxoethyl 6,11-dihydro-α-methyl-11-oxodibenz[b,e]oxepin-2-acetate.

ANALYSIS: Calculated for $C_{26}H_{22}O_6$: 72.55%C; 5.15%H; Found: 72.38%C; 5.27%H

EXAMPLE 14

(±)-Carboxymethyl 6,11-dihydro-α-methyl-11-oxodibenz[b,e]oxepin-2-acetate Hemihydrate A solution of 7.26 g (0.016 m) of (±)-2-phenylmethoxy-2-oxoethyl 6,11-dihydro-2-methyl-11-oxodibenz[b,e]oxepin-2-acetate of Example 13 in 150 ml ethyl acetate was hydrogenated in the presence of 0.72 g of Pd on carbon. After absorption of hydrogen stopped the catalyst was removed by filtration. Fresh catalyst was added (0.72 g) and the mixture hydrogenated until absorption of hydrogen ceased. The catalyst was removed by filtration and the filtrate was evaporated to give a crude oil which was purified by high pressure liquid chromatography giving 2 g (27%) of (±)-carboxymethyl 6,11-dihydro-α-methyl-11-oxodibenz[b,e]oxepin-2-acetate hemihydrate.

ANALYSIS: Calculated for $C_{19}H_{16}O_6 \cdot \frac{1}{2}H_2O$: 65.33%C; 4.91%H; Found: 65.72%C; 4.96%H

EXAMPLE 15

(±)-2-Methoxy-2-oxoethyl 6,11-Dihydro-α-methyl-11-oxodibenz[b,e]oxepin-2-acetate A stirred warm (55° C.) mixture of 6,11-dihydro-α-methyl-11-oxodibenz[b,e]oxepin-2-acetic acid (7.06 g, 0.025 mol), milled anhydrous $K_2CO_3$ (1.82 g, 0.13 mol) and sieved dried dimethylformamide (60 ml) was treated over a few minutes with methyl bromoacetate (4.13 g, 0.027 mol). After stirring overnight (about 16 hours) at 55° C. with exclusion of moisture, the mixture was decanted into water (300 ml) and extracted with ether (250 ml). The organic phase was washed with 5% $NaHCO_3$ solution and water, dried ($Na_2SO_4$), filtered and concentrated to afford an oil. A solution of the oil and benzene was filtered through anhydrous $Na_2SO_4$ and concentrated to afford an oil (6.45 g). The oil was purified by high pressure liquid chromatography (HPLC) and the appropriate fractions were combined and concentrated to afford an oil (4.29 g, 48.4%) of (±)-2-methoxy-2-oxoethyl 6,11-dihydro-α-methyl-11-oxodibenz[b,e]oxepin-2-acetate.

ANALYSIS: Calculated for $C_{20}H_{18}O_6$: 67.79%C; 5.12%H; Found: 67.74%C; 5.12%H

We claim:

1. A 6,11-dihydro-11-oxo-bibenz[b,e]oxepin derivative having the formula

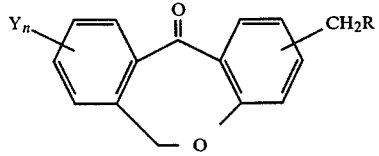

where Y is hydrogen, alkyl, alkoxy, halogen and trifluoromethyl; R is

where $R_{10}$ is hydrogen, and

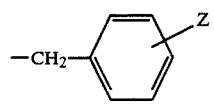

where Z is hydrogen, alkyl, alkoxy, halogen, trifluoromethyl, nitro and amino; and

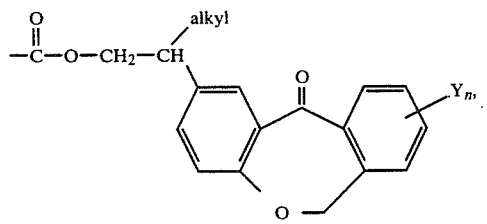

and where appropriate the optical isomers thereof and the racemic mixture thereof.

2. An antiinflammatory composition which comprises an effective antiinflammatory amount of a compound of the formula

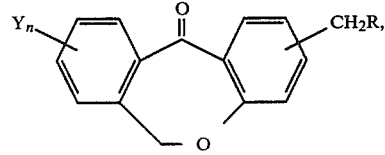

where Y is hydrogen, alkyl, alkoxy, halogen, and trifluoromethyl; R is

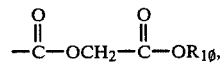

where $R_{10}$ is hydrogen and

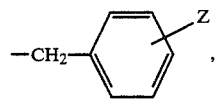

where Z is hydrogen, alkyl, alkoxy, halogen, trifluoromethyl, nitro and amino; and

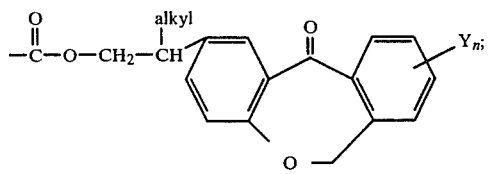

and where n is 0, 1, 2 or 3, and where appropriate the optical isomers thereof and the racemic mixture thereof.

3. An analgesic composition which comprises an effective pain alleviating amount of a compound of the formula

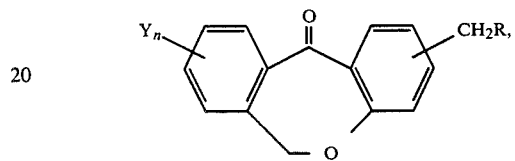

where Y is hydrogen, alkyl, alkoxy, halogen and trifluoromethyl; R is

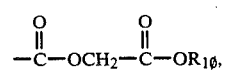

where $R_{10}$ is hydrogen and

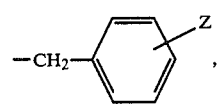

where Z is hydrogen, alkyl, alkoxy, halogen, trifluoromethyl, nitro and amino; and

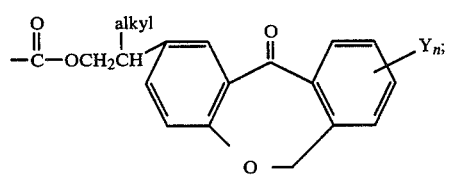

wherein n is 0, 1, 2 or 3 and where appropriate the optical isomers thereof and the racemic mixture thereof.

4. A 6,11-dihydrodibenz[b,e]oxepin acid derivative having the formula

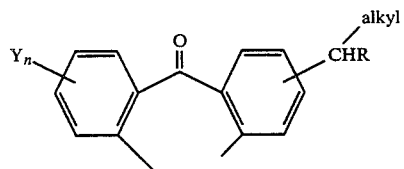

where Y is hydrogen, alkyl, alkoxy, halogen and trifluoromethyl; R is

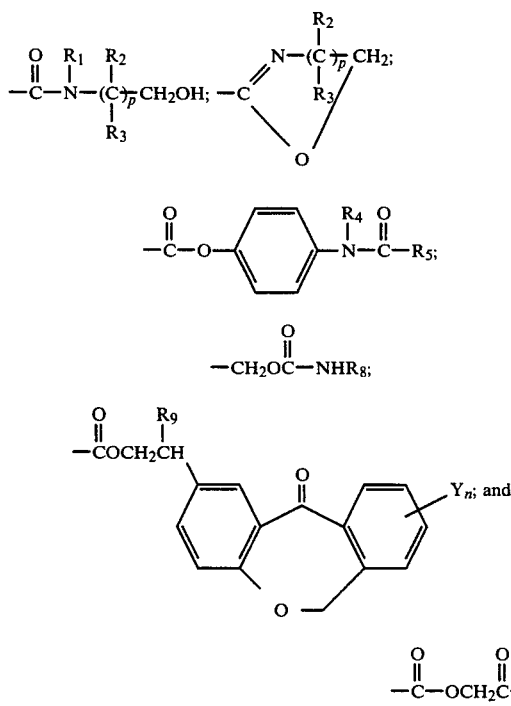

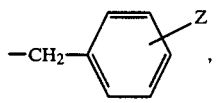

where $R_{10}$ is hydrogen, alkyl, and

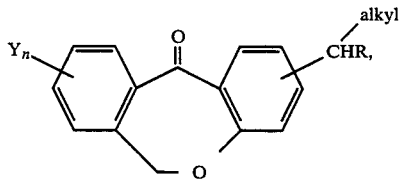

where Z is hydrogen, alkyl, alkoxy, halogen, trifluoromethyl, nitro and amino; where n is 0, 1, 2 or 3; p is 1 or 2; q is 0, 1, or 2; $R_1$ to $R_7$ are the same or different and are hydrogen and alkyl and $R_8$ is hydrogen, alkyl and phenyl; $R_9$ is hydrogen and alkyl; the optical isomers thereof and the racemic mixture thereof and the pharmaceutically acceptable addition salts thereof.

5. The compound as defined in claim 4 which is 2-phenylmethoxy-2-oxoethyl 6,11-dihydro-α-methyl-11-oxodibenz[b,e]-oxepin-2-acetate, or the optical isomers thereof or the racemic mixture thereof.

6. The compound as defined in claim 4 which is carboxymethyl 6,11-dihydro-α-methyl-11-oxodibenz[b,e]-oxepin-2-acetate or the optical isomers thereof or the racemic mixture thereof.

7. The compound as defined in claim 4 which is 2-methoxy-2-oxoethyl 6,11-dihydro-α-methyl-11-oxodibenz[b,e]oxepin-2-acetate, or the optical isomers thereof or the racemic mixture thereof.

8. An antiinflammatory composition which comprises an effective antiinflammatory amount of a compound of the formula

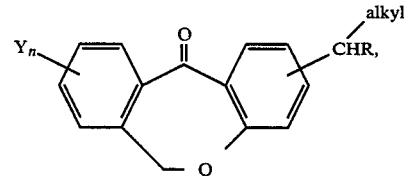

where Y is hydrogen, alkyl, alkoxy, halogen, and trifluoromethyl; R is

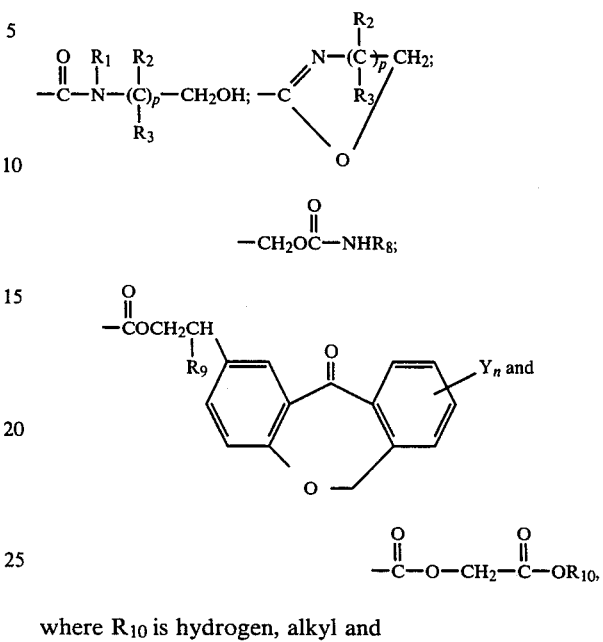

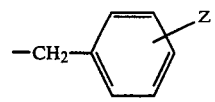

where $R_{10}$ is hydrogen, alkyl and

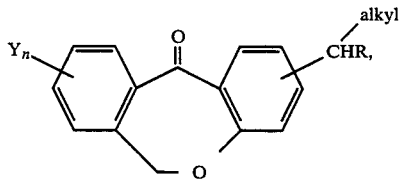

where Z is hydrogen, alkyl, alkoxy, halogen, trifluoromethyl, nitro and amino; where n is 0, 1, 2 or 3; p is 1 or 2; q is 0, 1, or 2; $R_1$ to $R_7$ are the same or different and are hydrogen and lower alkyl and $R_8$ is hydrogen, lower alkyl and phenyl and $R_9$ is hydrogen and alkyl, or its optical isomers of the racemic mixture thereof.

9. The composition as defined in claim 8 which comprises 2-phenylmethoxy-2-oxoethyl 6,11-dihydro-α-methyl-oxodibenz[b,e]-oxepin-2-acetate or the optical isomers thereof or the racemic mixture thereof.

10. The composition as defined in claim 8 which comprises carboxymethyl 6,11-dihydro-α-methyl-11-oxodibenz[b,e]-oxepin-2-acetate or the optical isomers thereof of the racemic mixture thereof.

11. The composition as defined in claim 7 which comprises 2-methoxy-2-oxoethyl 6,11-dihydro-α-methyl-11-oxodibenz[b,e]oxepin-2-acetate or the optical isomers thereof of the racemic mixture thereof.

12. An analgesic composition which comprises an effective pain alleviating amount of a compound of the formula

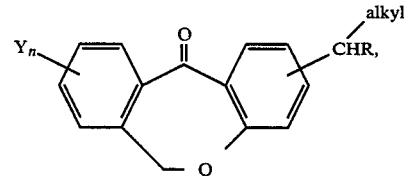

where Y is hydrogen, alkyl, alkoxy, halogen and trifluoromethyl; R is

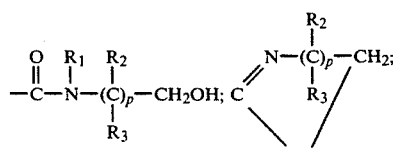

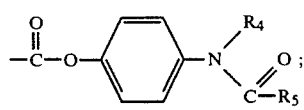

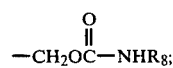

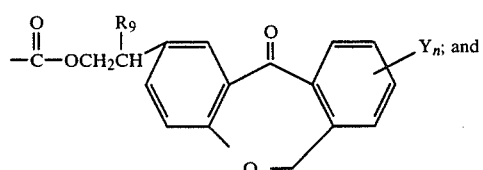

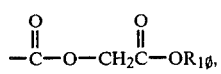

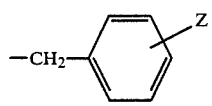

where $R_{10}$ is hydrogen, alkyl and

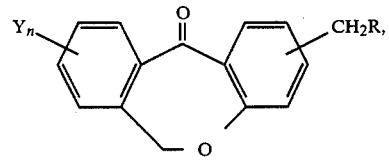

where Z is a hydrogen, alkyl, alkoxy, halogen, trifluoromethyl, nitro and amino; where n is 0, 1, 2 or 3; p is 1 or 2; q is 0, 1, or 2; $R_1$ to $R_7$ are the same or different and are hydrogen and lower alkyl, $R^8$ is hydrogen, lower alkyl and phenyl and $R_9$ is hydrogen and alkyl and where appropriate the optical isomers thereof and the racemic mixtures thereof.

13. The composition as defined in claim 12 which comprises 2-phenylmethoxy-2-oxoethyl 6,11-dihydro-α-methyl-11-oxodibenz[b,e]oxepin-2-acetate or the optical isomers thereof or the racemic mixture thereof.

14. The composition as defined in claim 12 which comprises carboxymethyl 6,11-dihydro-α-methyl-11-oxodibenz[b,e]oxepin-2-acetate or the optical isomers thereof of the racemic mixture thereof.

15. The analgesic composition as defined in claim 12 which comprises 2-methoxy-2-oxoethyl 6,11-dihydro-α-methyl-11-oxodibenz[b,e]oxepin-2-acetate or the optical isomers thereof of the racemic mixture thereof.

16. A method of alleviating inflammation in a mammal which comprises administering to a mammal an inflammation alleviating effective amount of a compound selected from the group consisting of (a) a compound of the formula

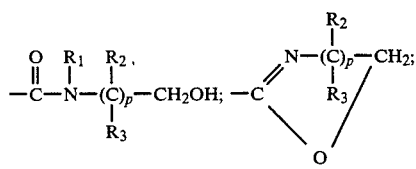

where Y is hydrogen, alkyl, alkoxy, halogen and trifluoromethyl; R is

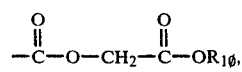

where $R_{10}$ is hydrogen and

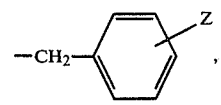

where Z is hydrogen, alkyl, alkoxy, halogen, trifluoromethyl, nitro and

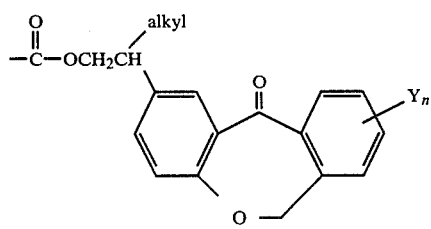

and where n is 0, 1, 2 or 3; and where appropriate the optical isomers thereof and the racemic mixture thereof; and (b) a compound of the formula

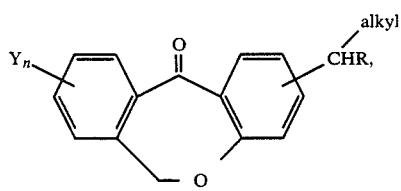

where Y is hydrogen, alkyl, alkoxy, halogen and trifluoromethyl; R is

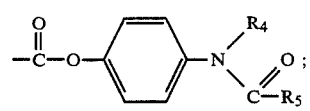

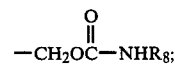

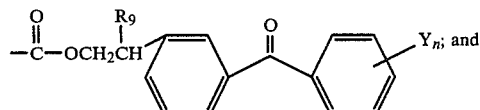

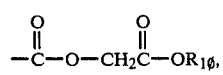

where $R_{10}$ is hydrogen, alkyl and

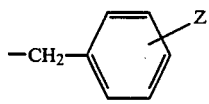

where Z is hydrogen, alkyl, alkoxy, halogen, trifluoromethyl, nitro and amino; where n is 0, 1, 2, 3; p is 1 or 2; q is 0, 1, or 2; $R_1$ to $R_7$ are the same or different and are hydrogen and lower alkyl, $R^8$ is hydrogen, lower alkyl and phenyl and $R_9$ is hydrogen and alkyl, or its optical isomers or the racemic mixture thereof.

17. A method of alleviating pain in a mammal which comprises administering for a mammal a pain alleviating effective amount of a compound selected from the group consisting of (a) a compound of the formula

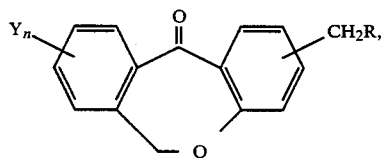

where Y is hydrogen, alkyl, alkoxy, halogen and trifluoromethyl; R is

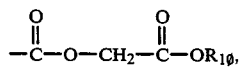

where $R_{10}$ is hydrogen and

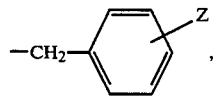

where Z is hydrogen, alkyl, alkoxy, halogen, trifluoromethyl, nitro and amino; and

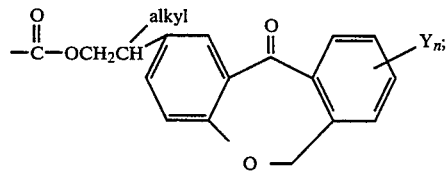

and where n is 0, 1, 2 or 3; and where appropriate the optical isomers thereof and the racemic mixture thereof; and (b) a compound of the formula

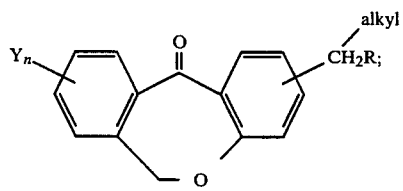

where Y is hydrogen, alkyl, alkoxy, halogen and trifluoromethyl; R is

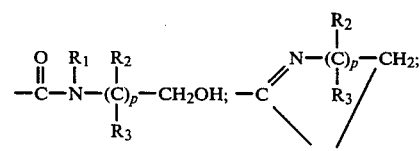

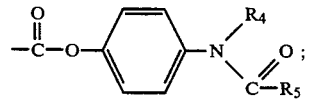

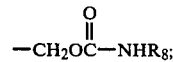

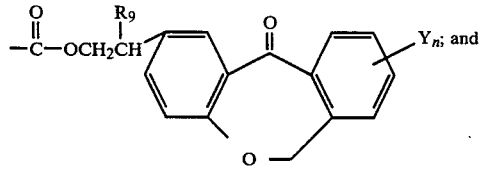

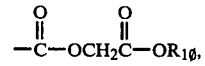

where $R_{10}$ is hydrogen, alkyl and

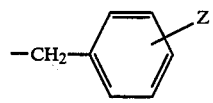

where Z is hydrogen, alkyl, alkoxy, halogen, trifluoromethyl, nitro and amino; where n is 0, 1, 2, 3; p is 1 or 2; q is 0, 1, or 2; $R_1$ to $R_7$ are the same or different and are hydrogen and lower alkyl, $R^8$ is hydrogen, lower alkyl and phenyl and $R_9$ is hydrogen and alkyl, or its optical isomers or the racemic mixture thereof.

* * * * *